(12) United States Patent
Iwasaka et al.

(10) Patent No.: US 9,188,842 B2
(45) Date of Patent: Nov. 17, 2015

(54) METHOD FOR MANUFACTURING LENS BARREL (75) Inventors: Kikuo Iwasaka, Iruma-gun (JP); Yuichi Atarashi, Hachioji (JP)

(73) Assignee: Konica Minolta, Inc., Tokyo (JP)

( * ) Notice: Subject to any disclaimer, the term of this patent is extended or adjusted under 35 U.S.C. 154(b) by 242 days.

(21) Appl. No.: 14/004,045

(22) PCT Filed: Feb. 15, 2012

(86) PCT No.: PCT/JP2012/053482
§ 371 (c)(1),
(2), (4) Date: Sep. 9, 2013

(87) PCT Pub. No.: WO2012/120981
PCT Pub. Date: Sep. 13, 2012

(65) Prior Publication Data
US 2013/0340234 A1 Dec. 26, 2013

(30) Foreign Application Priority Data
Mar. 7, 2011 (JP) ................................ 2011-048618

(51) Int. Cl.
| G02B 7/02 | (2006.01) |
| B23P 19/10 | (2006.01) |
| G03B 17/02 | (2006.01) |
| B25B 11/00 | (2006.01) |
| B23P 21/00 | (2006.01) |
| G02B 3/04 | (2006.01) |
| A61B 1/06 | (2006.01) |

(52) U.S. Cl.
CPC ................ G03B 17/02 (2013.01); B23P 19/10 (2013.01); B23P 21/004 (2013.01); B23P 21/006 (2013.01); B25B 11/005 (2013.01); G02B 3/04 (2013.01); G02B 7/027 (2013.01); A61B 1/0676 (2013.01); Y10T 29/49826 (2015.01)

(58) Field of Classification Search
CPC .................. Y10T 29/49998; Y10T 29/49829; Y10T 29/49899; B23P 21/004; B23P 21/006; B23P 19/10; B25B 11/005; B25B 11/02; B23Q 3/088; B23Q 3/186; G02B 7/02; A61B 1/0676
See application file for complete search history.

(56) References Cited

U.S. PATENT DOCUMENTS

| 7,289,282 B2 * | 10/2007 | Matsushima ................. 359/819 |
| 7,567,393 B2 * | 7/2009 | Chen et al. ..................... 359/809 |
| 2007/0007153 A1 * | 1/2007 | Watanabe et al. .......... 206/316.1 |

FOREIGN PATENT DOCUMENTS

| JP | 06-281851 | 10/1984 |
| JP | 59-176710 | 10/1984 |
| JP | 03-279239 | 12/1991 |
| JP | 04-125506 | 4/1992 |
| JP | 2006-220779 | 8/2006 |
| JP | 2009-116951 | 5/2009 |

* cited by examiner

Primary Examiner — Jermie Cozart
(74) Attorney, Agent, or Firm — Cozen O'Connor

(57) ABSTRACT

A manufacturing method of a lens barrel is disclosed. According to one implementation, the manufacturing method includes the following steps. A first lens holding section protrusion step inserts a first lens holding section from one end of a barrel frame to a hollow section to protrude from the other end. A second lens holding section suction step sucks a convex surface section. A first lens holding section contact step brings the planar surface section into contact with the first lens holding section. A lens holding switching step releases suction of the convex surface section, and the planar surface section is held by the first lens holding section. A barrel frame contact step moves the first lens holding section or the lens barrel so that a surrounding edge section is brought into contact with a lens receiving section.

9 Claims, 14 Drawing Sheets

METHOD FOR MANUFACTURING LENS BARREL

RELATED APPLICATIONS

This is a U.S. national stage of International application No. PCT/JP2012/053482 filed on Feb. 15, 2012.

This application claims the priority of Japanese application no. 2011-048618 filed Mar. 7, 2011, the entire content of which is hereby incorporated by reference.

FIELD OF THE INVENTION

TECHNICAL FIELD

The present invention relates to a method for manufacturing a lens barrel to manufacture a lens barrel by inserting a planar-convex lens into a barrel frame.

BACKGROUND ART

In a typical lens barrel for a camera, an outer diameter of a lens is relatively large, and therefore, the lens barrel is manufactured by holding a sidewall section of the lens with tweezers to drop the lens in a barrel frame. Alternatively, instead of using tweezers, a lens is held sucked by a suction pad by vacuuming air, and such suction of the lens is disclosed in various patent documents.

For example, in order to assemble an object lens to a barrel frame, there is known a configuration to suck the object lens on a tray, one by one, with the suction pad (see patent document 1).

Moreover, for the purpose of correction of position of an optical element, there is known a configuration to suck an optical element with a rubber buffer ring (see patent document 2).

PRIOR ART DOCUMENT

Patent Document

Patent Document 1: Japanese Unexamined Patent Application Publication No. 2009-116951

Patent Document 2: Japanese Unexamined Patent Application Publication No. 2006-220779

DISCLOSURE OF THE INVENTION

Problems to be Solved by the Invention

According to the above, as for the method of holding the lens with tweezers, if the lens is small, the area of contact with the tweezers becomes small, and there is a possibility that the tweezers slip so that it is not possible to securely hold the lens, resulting in the lens falling. Even if the lens does not fall, there is a possibility that the held lens tilts, and in such case, it is difficult to securely insert the lens in the barrel frame.

Further, for example, the lens used in illumination of an endoscope is no more than 1 mm, and it is very difficult to hold such a very small lens with tweezers. In addition, the lens is dropped to fall freely to be inserted in the barrel frame, however when the lens is a planar-convex lens, and is a hemisphere lens with a large curvature, even if it is intended to insert the lens so that the convex surface is the upper surface, since a center of gravity of the lens moves down with its own weight, the lens may rotate and turn sideways or upside down, resulting in the planar surface being the upper surface.

As described above, it is very difficult to use tweezers to hold a very small lens.

In view of the above, it is considered to use a suction device to suck the lens with the suction pad by vacuuming air. With this, it is possible to securely hold and move the lens even if the lens is very small.

However, when the convex surface of the planar-convex lens with the large curvature is sucked by a suction pad, the optical axis of the planar-convex lens and the inserting direction to the barrel frame are often misaligned by the attitude that the planar-convex lens is placed in the tray. As a result, the planar-convex lens is inserted tilted in the barrel frame, and the lens barrel may become a defective lens barrel with poor optical performance. Moreover, depending on the degree of the tilt, it may not be possible to insert the lens in the barrel frame. Further, when the suction of the planar-convex lens is released above the barrel frame and the planar-convex lens is dropped to fall freely, the above problem is aggravated due to the weight of the lens.

The present invention has been conceived in view of the above problems, and the present invention relates to a method for manufacturing a lens barrel where a planar-convex lens is inserted in a barrel frame, and it is an object of the present invention to provide a method for manufacturing a lens barrel where it is possible to securely insert a planar-convex lens in a barrel frame without tilting.

The above described patent documents 1 and 2 do not describe the above problems which occur when the planar-convex lens is inserted in the barrel frame.

Means for Solving the Problem

The above object can be achieved by the invention described below.

1. A manufacturing method of a lens barrel in which a first lens holding section which can hold a planar surface section of a planar-convex lens and a second lens holding section which can suck a convex surface section of the planar-convex lens are used to insert the planar-convex lens in a hollow section provided in a barrel frame, the manufacturing method comprising:

a first lens holding section protrusion step in which the first lens holding section is inserted from an opening section positioned at one end of the barrel frame to the hollow section to protrude the first lens holding section from an opening section positioned at the other end of the barrel frame;

a second lens holding section suction step in which the convex surface section of the planar-convex lens is sucked with the second lens holding section;

a first lens holding section contact step in which the planar surface section of the planar-convex lens is brought into contact with the first lens holding section after the first lens holding section protrusion step and the second lens holding section suction step;

a lens holding switching step in which suction of the convex surface section of the convex-planar lens is released by the second lens holding section, and the planar surface section of the planar-convex lens is held by the first lens holding section after the first lens holding section contact step; and a barrel frame contact step in which the first lens holding section or the lens barrel is moved in an optical axis direction of the planar-convex lens so that a surrounding edge section of the planar surface section of the planar-convex lens is brought into contact with a lens receiving section provided in the hollow section of the barrel frame after the lens holding switching step.

2. The manufacturing method of a lens barrel of claim 1, wherein the second lens holding section suction step is performed after the first lens holding section protrusion step.

3. The manufacturing method of a lens barrel of claim 1, wherein the first lens holding section protrusion step is performed after the second lens holding section suction step.

4. The manufacturing method of a lens barrel of claim 1, wherein the second lens holding section suction step is performed simultaneously with the first lens holding section protrusion step.

5. The manufacturing method of a lens barrel of any one of claims 1 to 4, wherein the planar-convex lens includes a side wall section formed between the convex surface section and the planar surface section parallel to an optical axis, and the side wall section is fitted to an inner surrounding wall of the hollow section of the barrel frame.

6. The manufacturing method of a lens barrel of any one of claims 1 to 5, further comprising a bonding step in which the planar-convex lens is bonded to the barrel frame after the barrel frame contact step.

7. The manufacturing method of a lens barrel of claim 6, wherein the planar-convex lens includes a side wall section formed between the convex surface section and the planar surface section parallel to an optical axis, and adhesive is filled between the side wall section and the inner surrounding wall.

8. The manufacturing method of a lens barrel of any one of claims 1 to 7, wherein the first lens holding section can suck the planar surface section of the planar-convex lens.

9. The manufacturing method of a lens barrel of claim 8, wherein vacuuming power of the first lens holding section is stronger than vacuuming power of the second lens holding section.

Advantageous Effect of the Invention

According to the method for manufacturing the lens barrel of the present invention, the planar-convex lens can be securely inserted in the barrel frame without tilting the planar-convex lens, when the planar-convex lens is inserted in the barrel frame.

EMBODIMENT FOR CARRYING OUT THE INVENTION

The method for manufacturing the lens barrel according to the present invention is described in detail with reference to the drawings.

Figure 1:
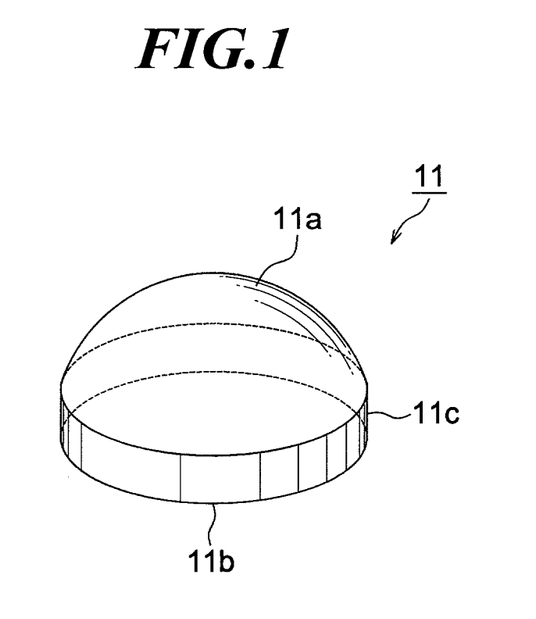
FIG. 1 is a perspective view of a planar-convex lens.
Figure 2:
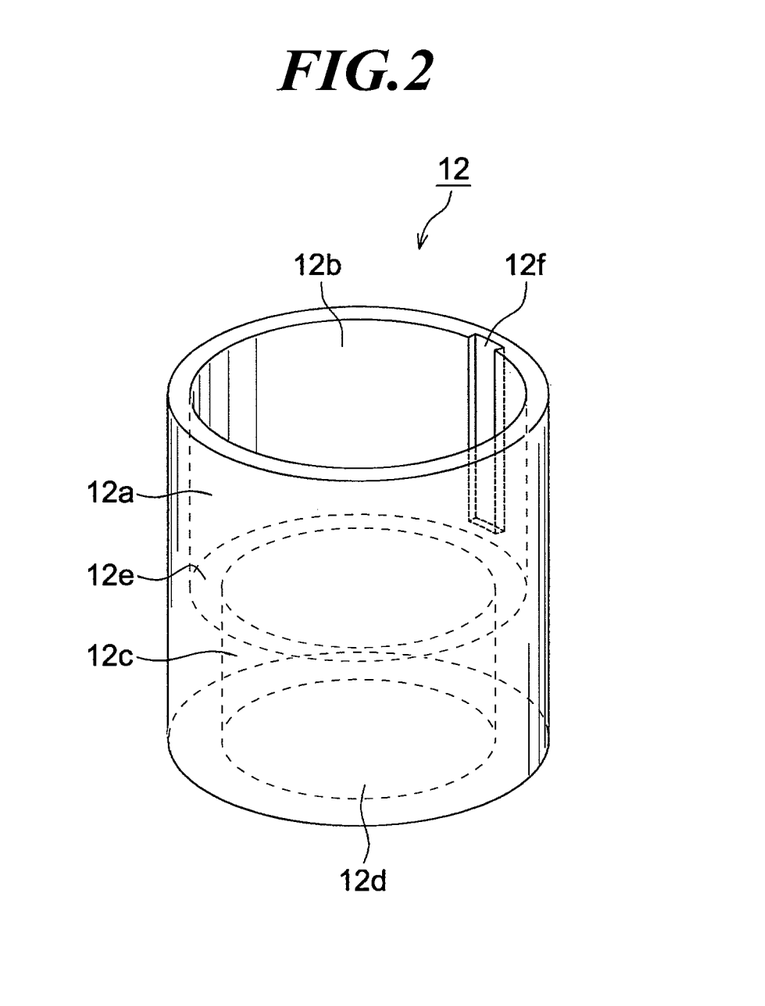
FIG. 2 is a perspective view of a barrel frame.

FIG. 1 is a perspective view of a planar-convex lens, and FIG. 2 is a perspective view of a barrel frame.

The lens barrel is completed by combining the planar-convex lens 11 shown in FIG. 1 with the barrel frame 12 shown in FIG. 2. The lens barrel is used in, for example, illumination of an endoscope, or illumination of a diagnosis probe inserted in a forceps channel of an endoscope to be provided for internal diagnosis. The lens barrel has a very small dimension and is manufactured in large numbers. Therefore, the lens barrel is usually manufactured using an automatic assembling device instead of manufacturing by hand.

As shown in FIG. 1, the planar-convex lens 11 includes a convex surface section 11a formed in a hemisphere shape, a planar surface section 11b formed in a planar surface opposite to the convex surface section 11a, and a surrounding wall section (side wall section) 11c formed between the convex surface section 11a and the planar surface section 11b and parallel to the optical axis. The material of the planar-convex lens 11 may be resin or glass.

As shown in FIG. 2, the lens barrel 12 is formed in a cylinder shape, and a first hollow section 12a and a second hollow section 12c penetrates the lens barrel 12. The inner diameter of the first hollow section 12a is larger than that of the second hollow section 12c. The step between the first hollow section 12a and the second hollow section 12c functions as a lens receiving section 12e which holds a surrounding edge section of the planar section 11b of the planar-convex lens 11 as described later. As described later, a groove section 12f to drop adhesive is formed in an inner surrounding wall of the first hollow section 12a.

When the lens barrel is used for the purpose of illuminating inside a lumen of a live body with light of illuminating optical fiber not shown positioned in, for example a tip of the endoscope or a tip of the diagnosis probe inserted in the forceps channel of the endoscope to be provided for internal diagnosis, the lens barrel 12 is formed by a transparent resin.

Figure 3:
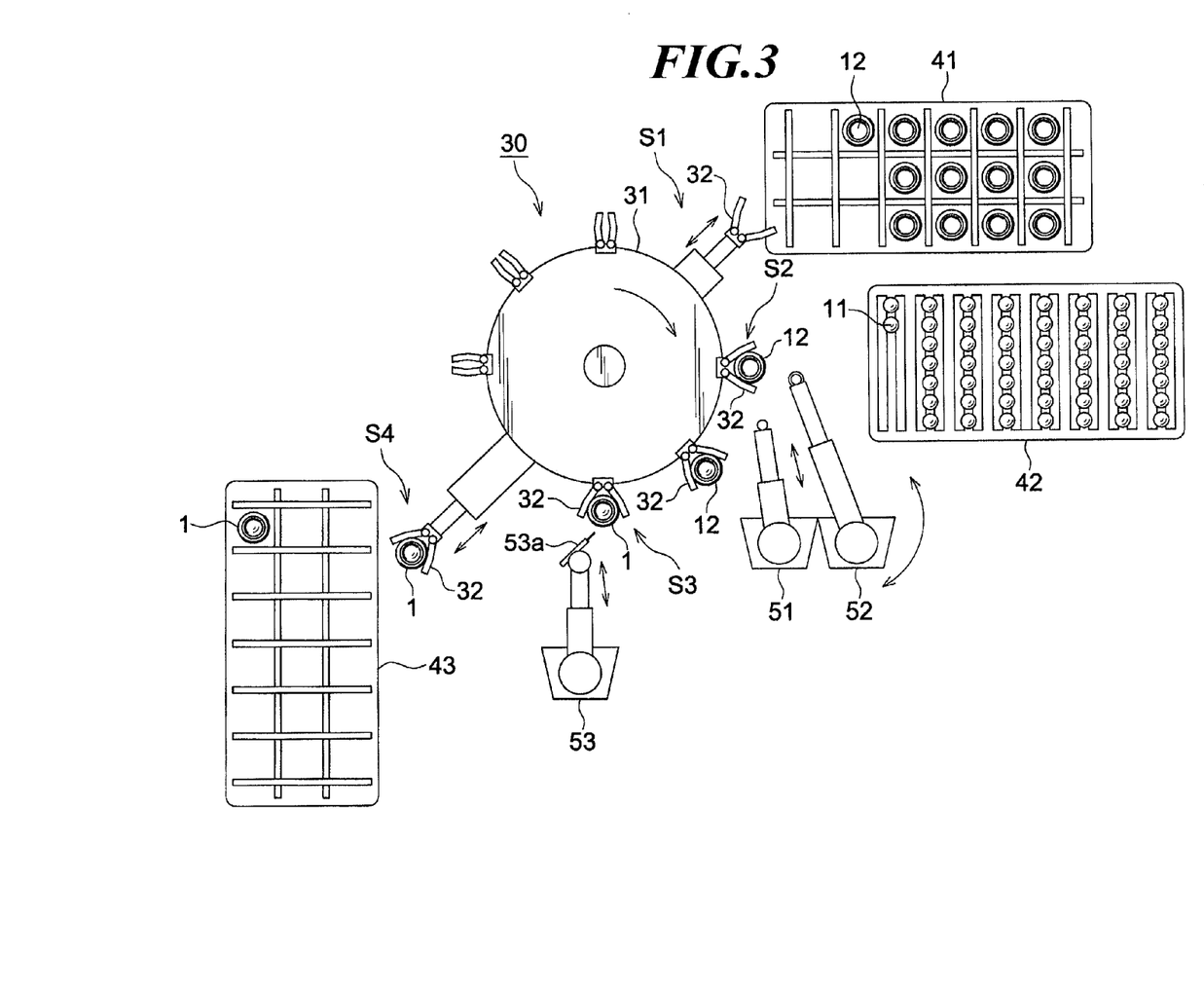
FIG. 3 is a schematic view of a step of manufacturing a lens barrel with an automatic assembling device viewed from above.

FIG. 3 is a schematic diagram showing a step of manufacturing the lens barrel with the automatic assembling device viewed from above.

The automatic assembling device 30 used in this step is a rotary type and includes a plurality of stations and intermittently rotates in a clockwise direction. Below, the operation is described for each station.

[First Station]

The first station S1 holds the lens barrel 12.

A plurality of robot arms 32 are provided to a rotation table 31 of the automatic assembling device 30 to extend and contract in a radiation direction.

Moreover, a plurality of barrel frames 12 are placed on a barrel frame tray 41 near the first station S1. The barrel frame 12 is placed in an attitude so that the first hollow section 12a is positioned above the second hollow section 12c as shown in FIG. 2.

Figure 4:
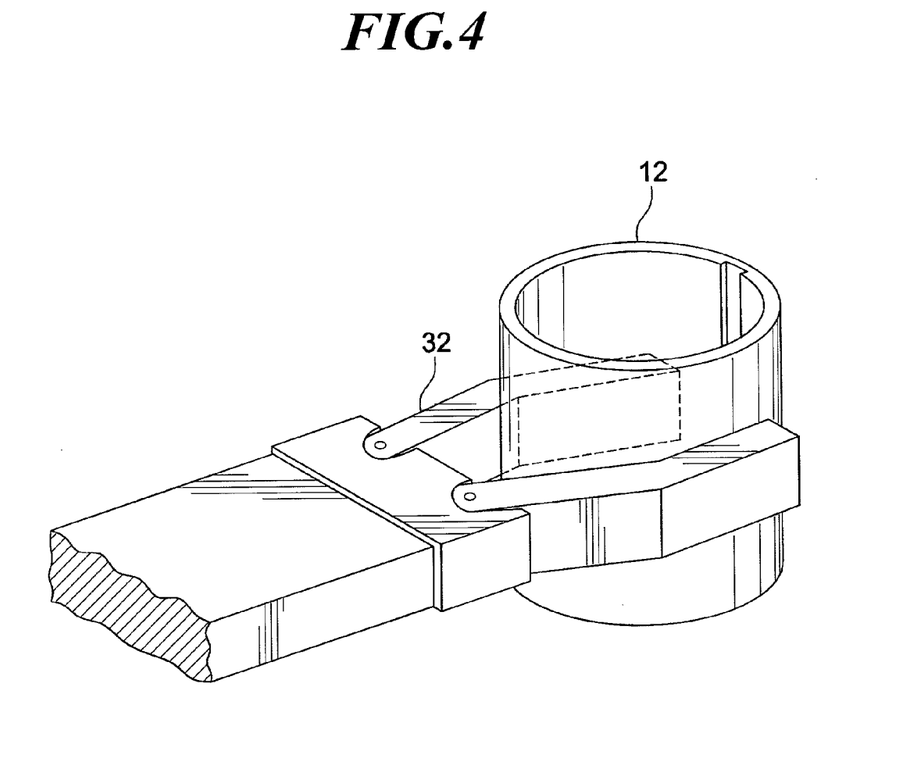
FIG. 4 is a perspective view of a robot arm holding the barrel frame.

Then, as shown in the perspective view of FIG. 4, the robot arm 32 holds any of the barrel frames 12 and conveys the barrel frame 12 to the second station S2.

Here, the barrel frame tray 41 may be fixed, and the robot arm 32 may suitably move above the barrel frame tray 41, or the barrel frame tray 41 may move in a planar direction of front, back, left, and right so that the robot arm 32 can easily hold the barrel frame 12.

The rotation of the rotating table 31 and the extension and contraction movement of the robot arm 32 are controlled by an imaging device or a CPU which are not shown.

[Second Station]

In the second station S2, the planar-convex lens 11 is inserted in the barrel frame 12.

Next, a first suction device 51 and a second suction device 52 which take in air are provided near the second station S2, and a suction pad which has a vacuuming opening and which is made from rubber, etc. is provided at each tip. The first suction device 51 and the second suction device 52 are driven with control by the CPU which is not shown. The suction pad is suitably moved in a horizontal direction and a vertical direction as shown in FIG. 3, and starts and stops vacuuming of air.

The first suction device 51 and the second suction device 52 include an evacuated state generator which is not shown. Compressed air is flown in the evacuated state generator to generate an evacuated portion, and air is vacuumed from the suction pad. The start and stop of the vacuuming is performed by a solenoid valve.

Figure 5:
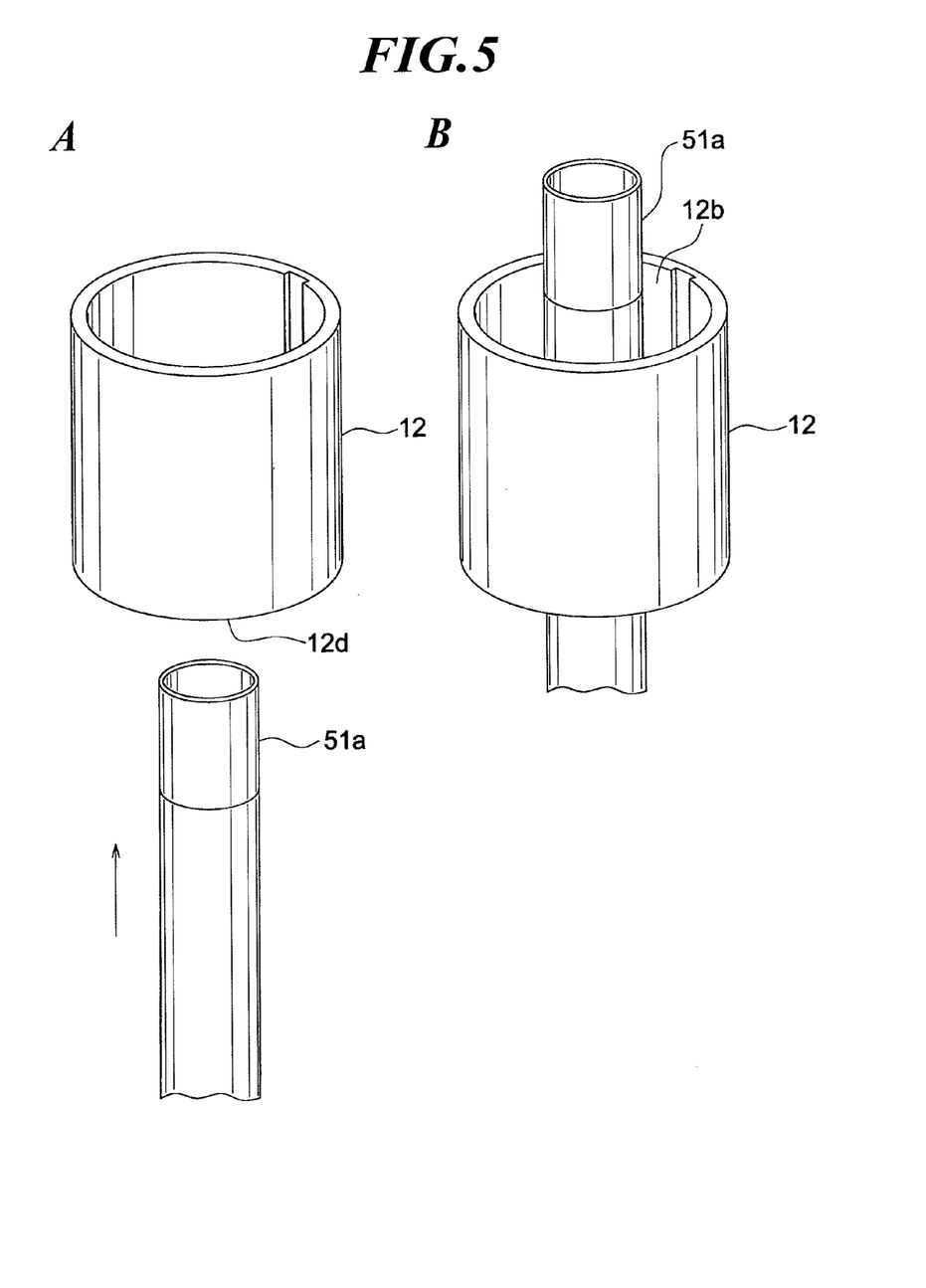
FIG. 5 is a perspective view showing a step of inserting a suction pad of a first suction device in the barrel frame.

When the barrel frame 12 is moved to the second station S2 by the robot arm 32, a suction pad 51a (first lens holding section) of the first suction device 51 is inserted from an opening section positioned at one end of the barrel frame 12, in other words, the opening section 12d of the second hollow section 12c positioned at the bottom as shown in the "A" portion of FIG. 5. Then, the suction pad 51a protrudes from the opening section positioned on the other end of the barrel frame 12, in other words, the opening section 12b of the first hollow section 12a positioned at the top as shown in the "B" portion of FIG. 5 (first lens holding section protrusion step).

An outer diameter of the suction pad 51a is formed rather smaller than the inner diameter of the second hollow section 12c.

FIG. 5 and the subsequent diagrams are illustrated without the robot arm 32.

Figure 6:
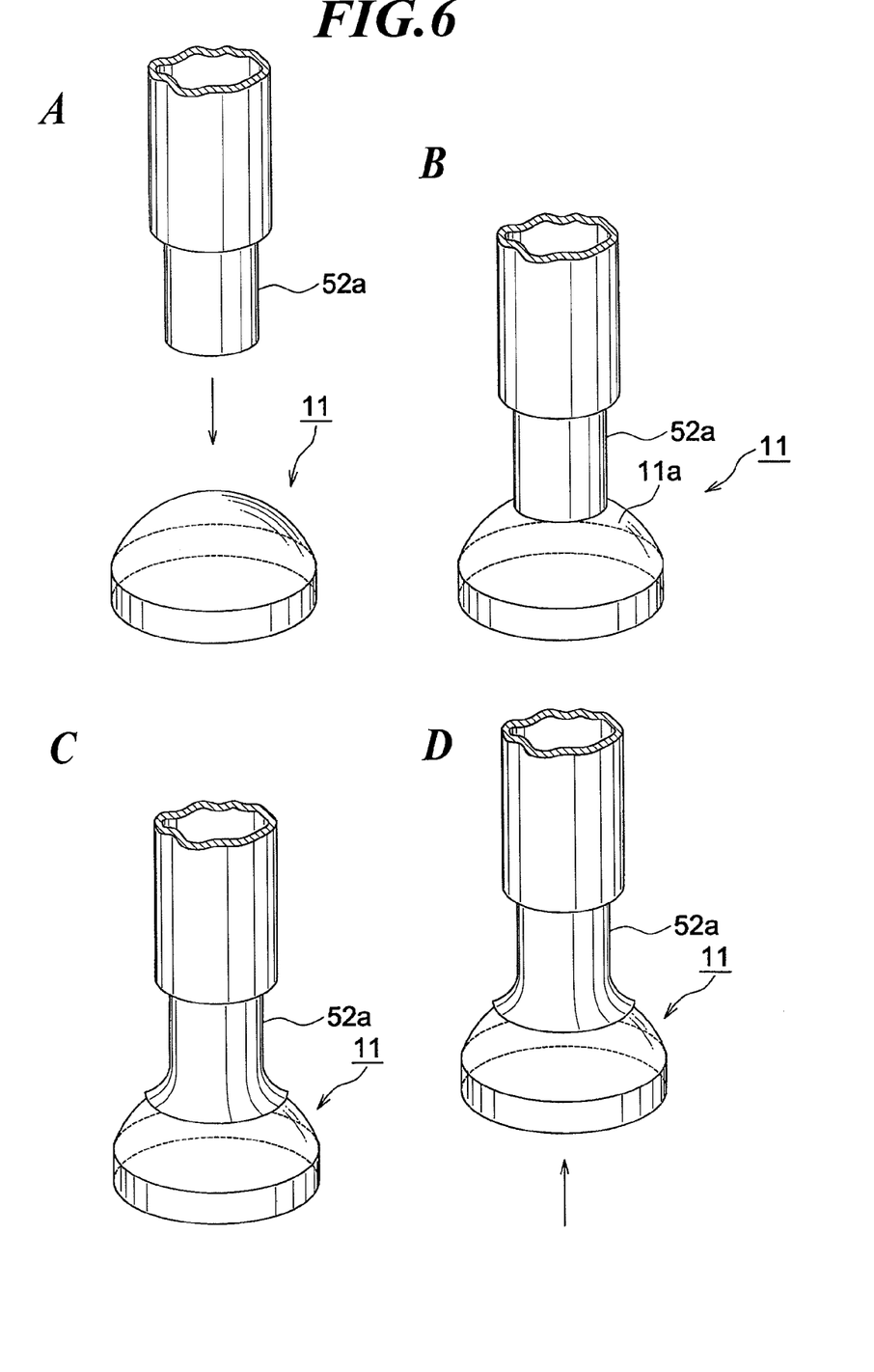
FIG. 6 is a perspective view showing a step of sucking the planar-convex lens with the suction pad of the second suction device.

Next, the suction pad 52a (second lens holding section) of the second suction device 52 is operated to suck the convex surface section 11a of the planar-convex lens 11 (second lens holding section suction step) as shown in FIG. 6.

The present embodiment shows an example of performing the "first lens holding section protrusion step" and then the "second lens holding section suction step", however, the order of the steps can be reversed or the steps can be performed substantially simultaneously.

As shown in FIG. 3, a plurality of planar-convex lenses 11 are placed with the convex surface section 11a upward on a lens tray 42 near the first station S2. The second suction device 52 is rotatable and the suction pad 52a can move forward and backward. As shown in the "A" portion of FIG. 6, the suction pad 52a is moved above any of the planar-convex lenses 11, and as shown in the "B" portion of FIG. 6, the suction pad 52a is brought into contact with the convex surface section 11a of the planar-convex lens 11. Then, the second suction device 52 performs the vacuuming operation, and as shown in the "C" portion of FIG. 6, the planar-convex lens 11 is sucked by the suction pad 52a. Then, as shown in the "D" portion of FIG. 6, the suction pad 52a sucking the planar-convex lens 11 is moved above the lens tray 42.

Figure 14:
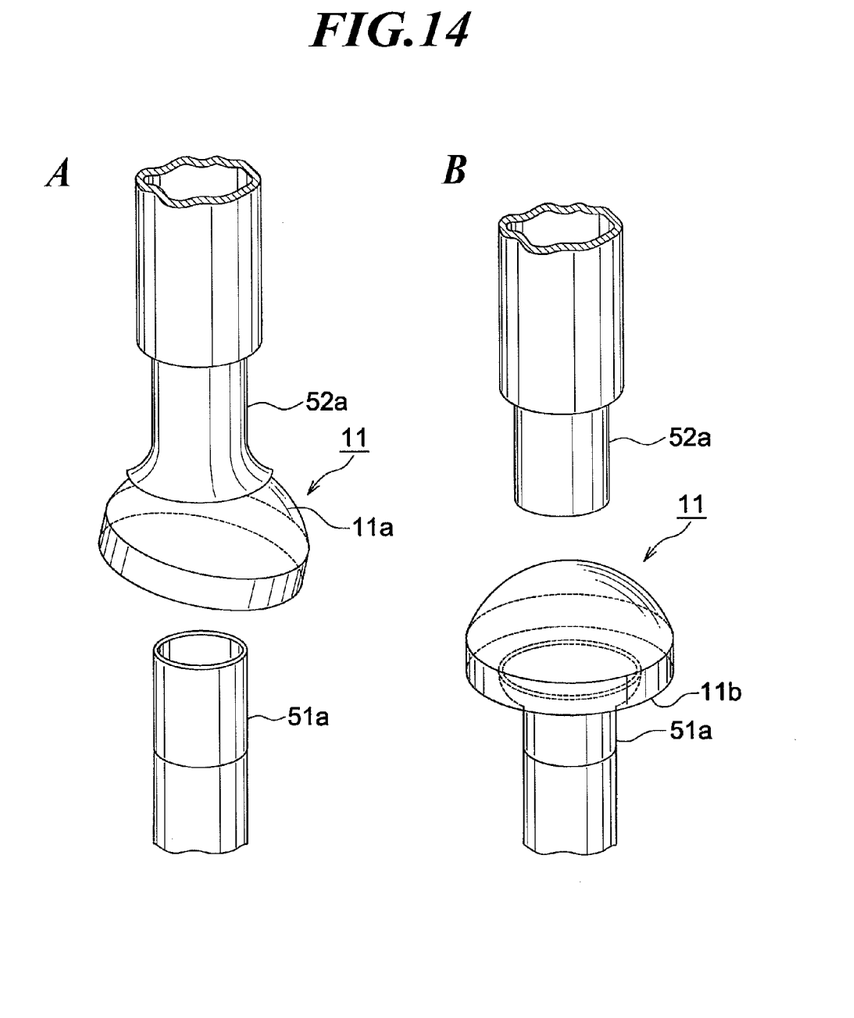
FIG. 14 is a perspective view showing that the planar-convex lens is corrected even if the planar-convex lens is sucked by the second suction device in a tilted state.

Here, even if the suction pad 52a sucks the convex surface section 11a of the planar-convex lens 11 in a state where the planar-convex lens 11 is slightly tilted, as described later with reference to FIG. 14, the suction pad 51a sucks the planar surface section 11b of the planar-convex lens 11, and therefore, there is no problem.

Here, the lens tray 42 may be fixed, and the suction pad 52a may suitably move above the lens tray 42, or the lens tray 42 may move in a planar direction of front, back, left, and right so that the suction pad 52a can easily suck the planar-convex lens 11.

Figure 7:
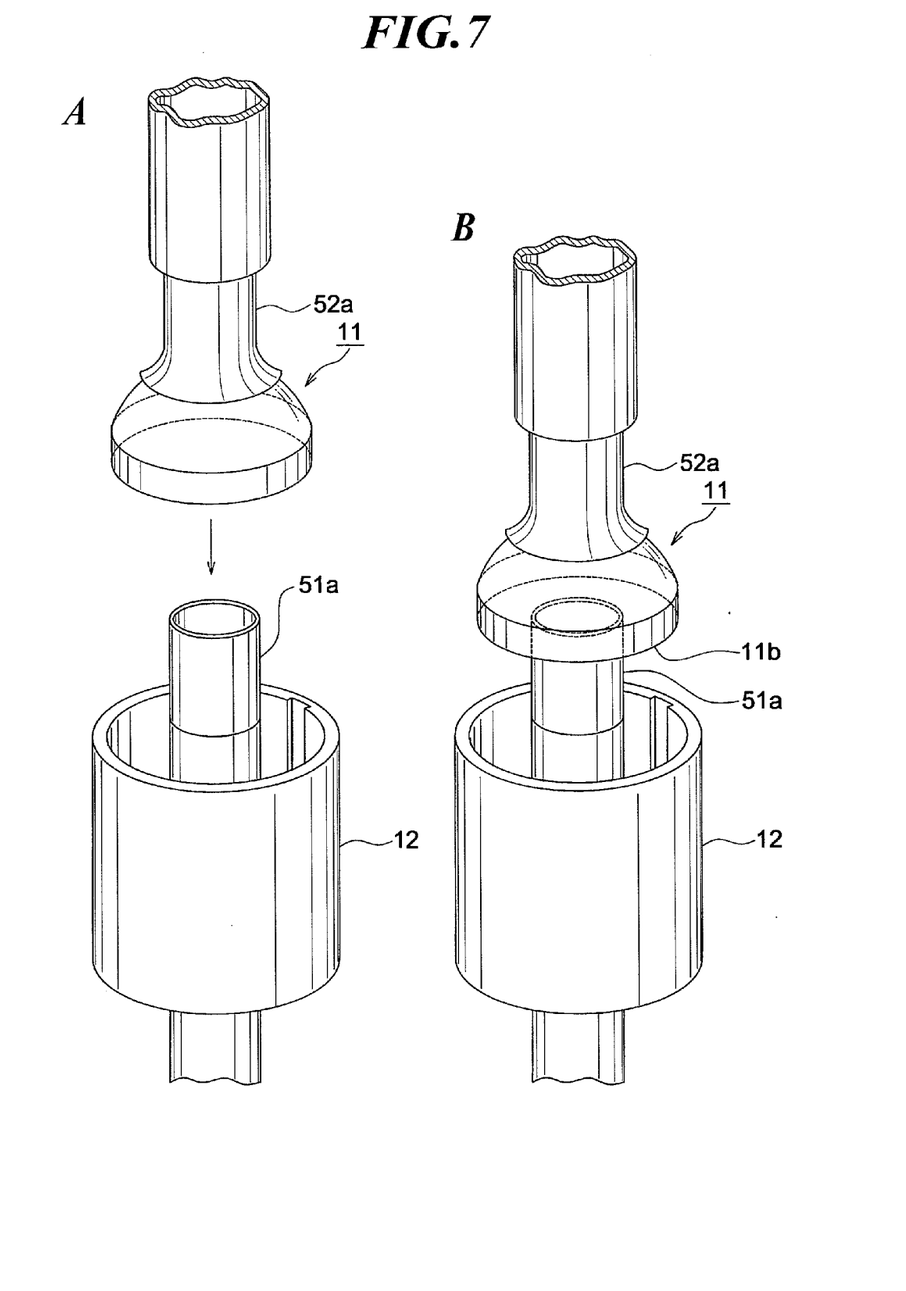
FIG. 7 is a perspective view showing a step of bringing the planar-convex lens in contact with the suction pad of the first suction device.

Next, as shown in the "A" portion of FIG. 7, the second suction device 52 moves with the suction pad 52a sucking the planar-convex lens 11, and draws near the suction pad 51a protruding from the barrel frame 12 from above. Then, as shown in the "B" portion of FIG. 7, the planar section 11b of the planar-convex lens 11 is brought into contact with the suction pad 51a (first lens holding section contact step).

Figure 8:
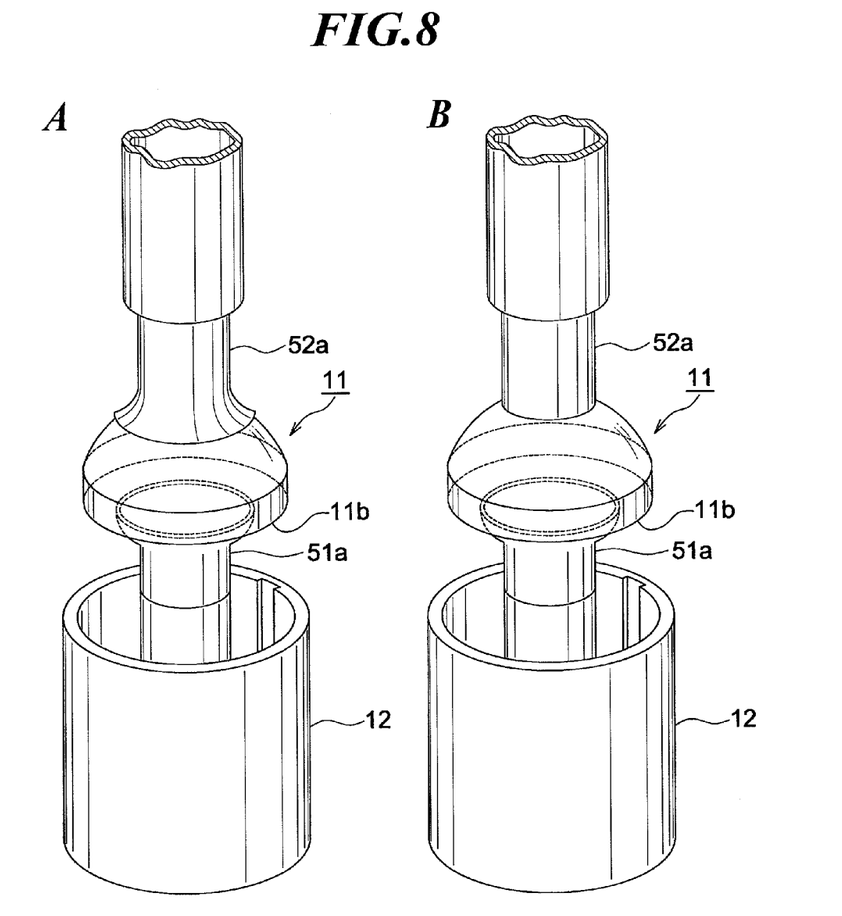
FIG. 8 is a perspective view showing a step of sucking the planar-convex lens with the suction pad of the first suction device.

Next, as shown in the "A" portion of FIG. 8, the first suction device 51 performs the vacuuming operation and the suction pad 51a sucks the planar section 11b of the planar-convex lens 11. Then, as shown in the "B" portion of FIG. 8, the second suction device 52 stops the vacuuming operation.

Figure 9:
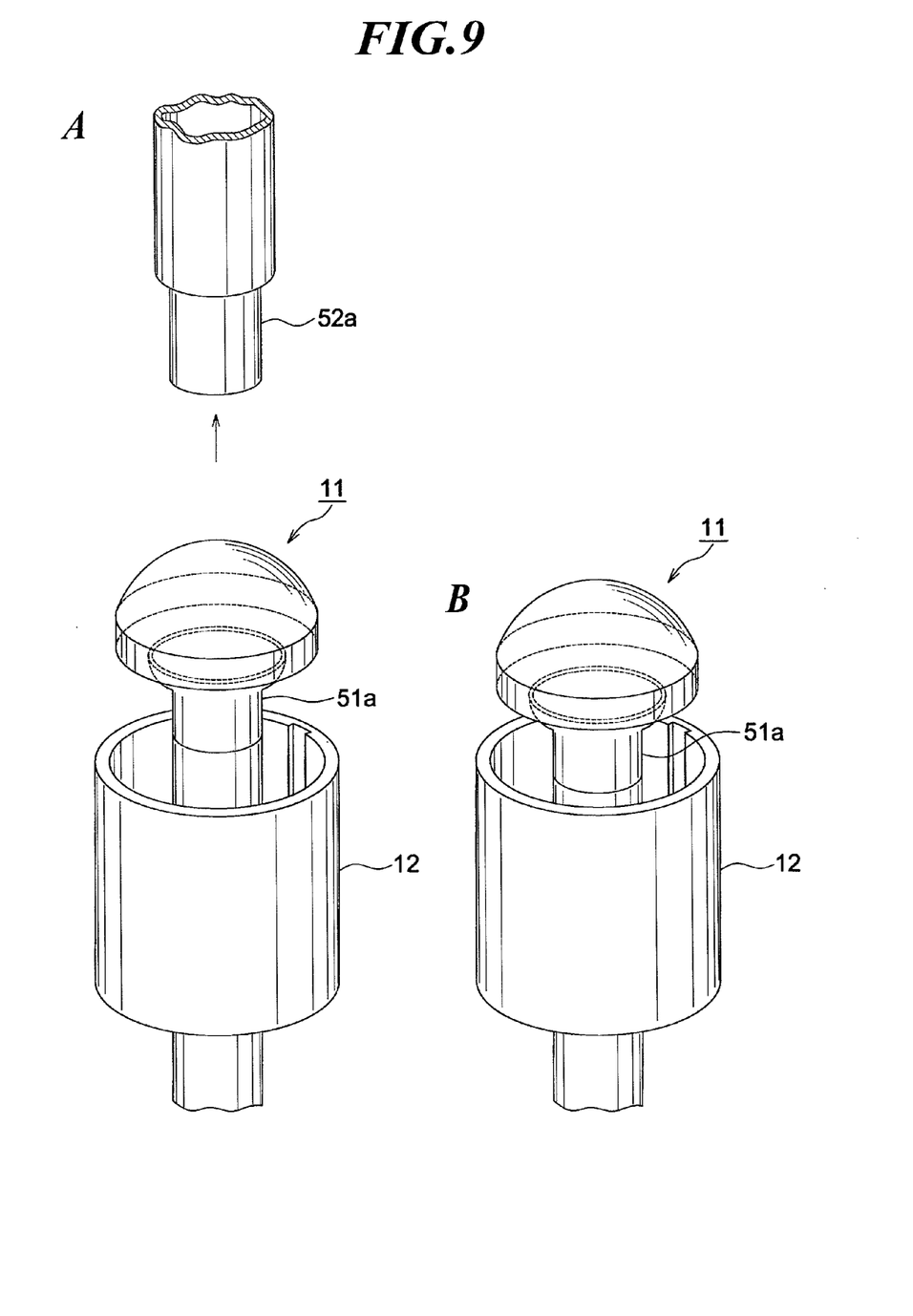
FIG. 9 is a perspective view showing a step of sucking the planar-convex lens with the suction pad of the first suction device.

Then, as shown in the "A" portion of FIG. 9, when the suction pad 52a of the second suction device 52 is moved away upward, the planar-convex lens 11 is sucked by the suction pad 51a. In other words, the suction pad holding the planar-convex lens 11 is switched from the suction pad 52a to the suction pad 51a (lens holding switching step).

In this state, the first suction device 51 is operated to move the suction pad 51a in the horizontal direction while imaging the planar-convex lens 11 and the barrel frame 12 with the imaging device not shown, and an optical axis of the planar-convex lens 11 is matched with a central axis of the barrel frame 12 based on image acknowledgement as shown in the "B" portion of FIG. 9. As a method to match the optical axis of the planar-convex lens 11 and the central axis of the barrel frame 12, other than matching the optical axis by acknowledging the image and using the automatic device, an operator can perform matching by confirming by sight and operating manually.

Then, the first suction device 51 is operated, the suction pad 51a protruding from the barrel frame 12 is moved downward, the suction pad 51a is moved through the first hollow section 12a and into the second hollow section 12c of the barrel frame 12, and the planar-convex lens 11 is inserted in the first hollow section 12a of the barrel frame 12. Then, as shown in the "A" portion of FIG. 10, the surrounding edge section of the planar section 11b of the planar-convex lens 11 is brought into contact with the lens receiving section 12e of the barrel frame 12 (barrel frame contact step). Here, the surrounding wall section 11c of the planar-convex lens 11 can be fitted in the inner surrounding wall of the first hollow section 12a of the barrel frame 12.

Figure 10:
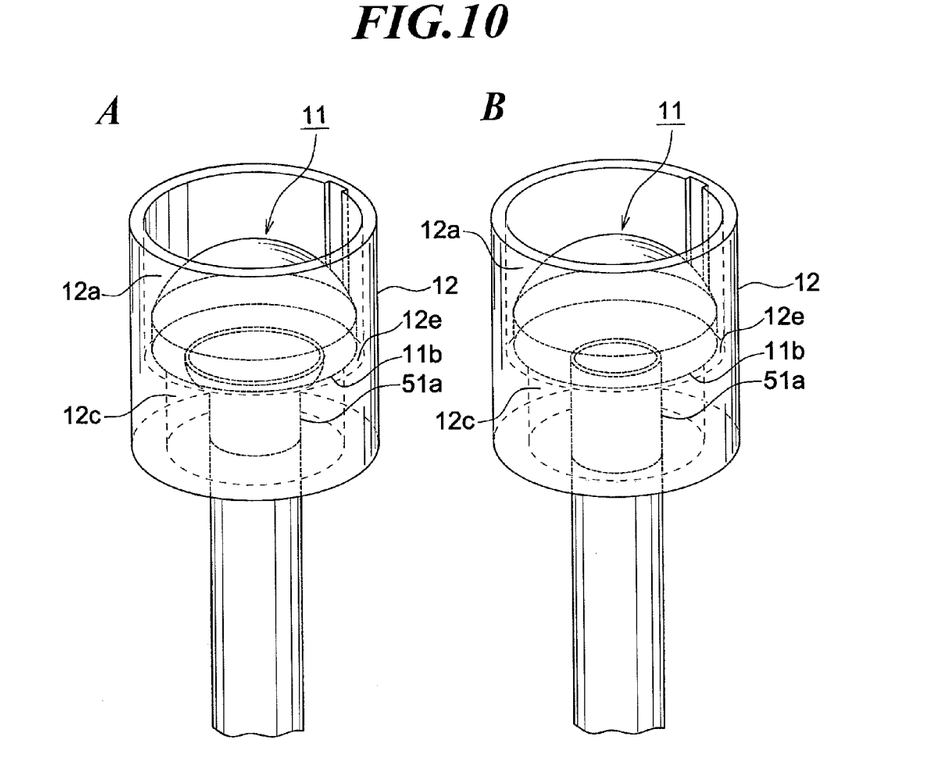
FIG. 10 is a perspective view showing a step of bringing the planar surface section of the planar-convex lens in contact with a lens receiving section of the barrel frame.

If the barrel frame 12 is transparent, it is possible to easily detect with the imaging device when the planar section 11b of the planar-convex lens 11 comes into contact with the lens receiving section 12e of the barrel frame 12. If the barrel frame 12 is not transparent, the above state is detected by resistance generated while the suction pad 51a is moved.

Figure 11:
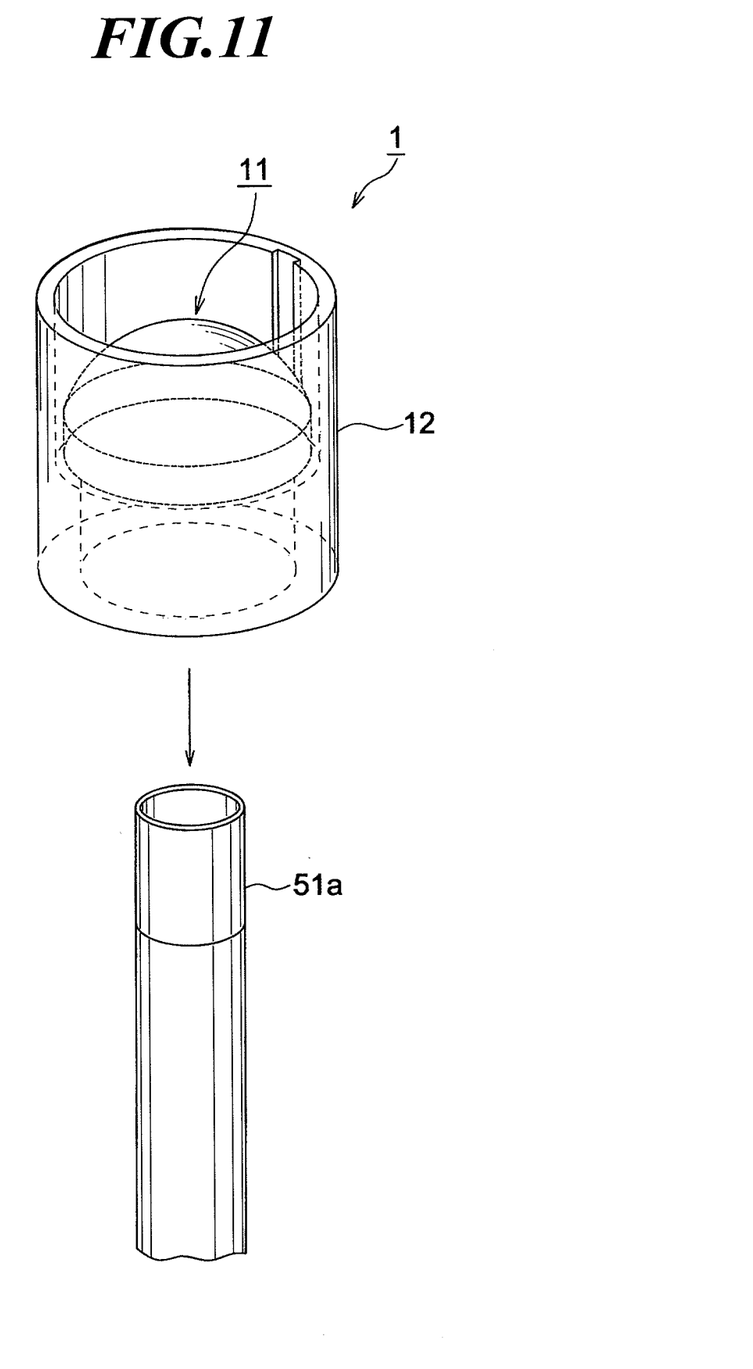
FIG. 11 is a perspective view showing a step of moving away the suction pad of the first suction device from the barrel frame.
Figure 12:
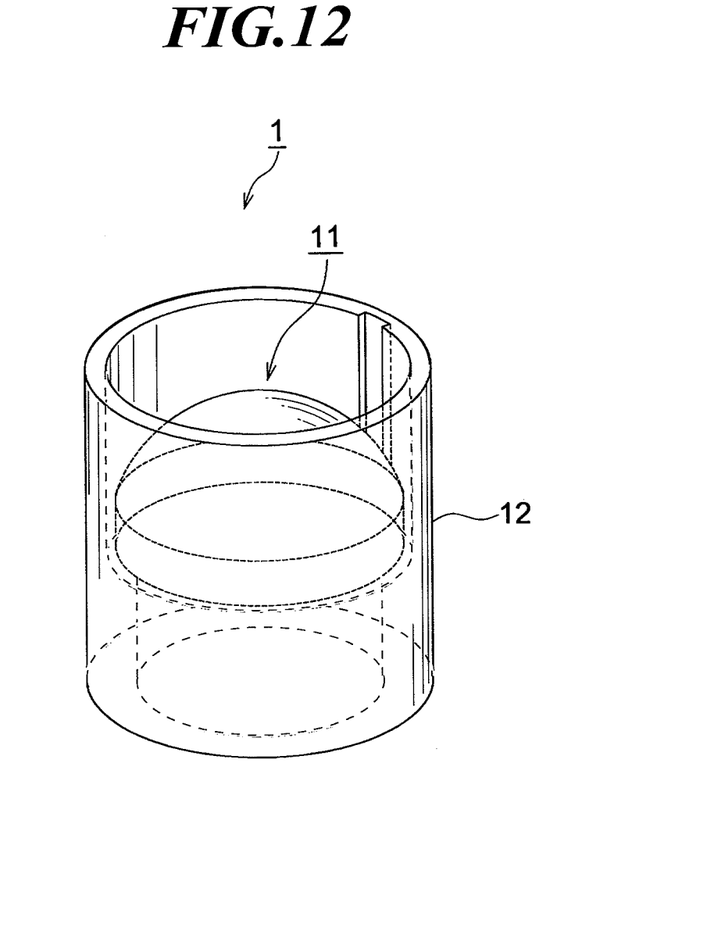
FIG. 12 is a perspective view of the lens barrel.

When the planar section 11b of the planar-convex lens 11 comes into contact with the lens receiving section 12e of the barrel frame 12, as shown in the "B" portion of FIG. 10, the first suction device 51 stops the vacuuming operation. Then, as shown in FIG. 11, the suction pad 51a of the first suction device 51 is moved away from the barrel frame 12. With this, as shown in FIG. 12, the lens barrel 1 with the planar-convex lens 11 inserted in the barrel frame 12 is completed.

Then, the robot arm 32 holds the lens barrel 1, and the lens barrel 1 is conveyed to the third station S3.

In the step of inserting the suction pad 51a from the bottom of the barrel frame 12 and protruding the suction pad 51a from the top, the suction pad 51a may be moved with the barrel frame 12 fixed, or the barrel frame 12 can be moved from the top toward the bottom with the suction pad 51a fixed.

In the step of moving the suction pad 51a downward in the optical axis direction to bring the planar surface section 11b of the planar-convex lens 11 in contact with the lens receiving section 12e of the barrel frame 12, the barrel frame 12 can be moved upward with the suction pad 51a fixed.

If the vacuuming power of the suction pad 51a of the first suction device 51 is made stronger than the vacuuming power of the suction pad 52a of the second suction device 52, the planar-convex lens 11 can more reliably move to the suction pad 51a, and it is possible to switch the holding of the planar-convex lens 11 without having to perform operation to stop the vacuum of the suction device. It is also possible to move the planar-convex lens 11 from the suction pad 52a to the suction pad 51a before the second suction device 52 stops the vacuuming operation.

In addition, the operation of the first suction device 51 and the second suction device 52 is controlled by the CPU which is not shown.

[Third Station]

Figure 13:
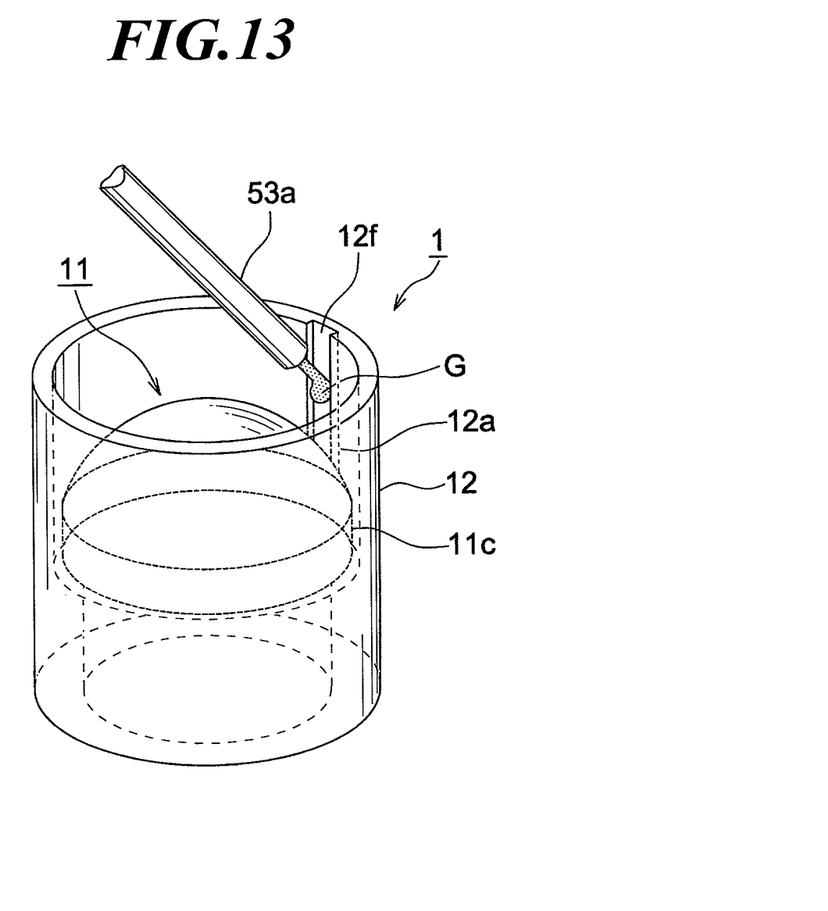
FIG. 13 is a perspective view showing a step of dropping an adhesive in a groove section of the lens barrel.

When the barrel frame 12 moves to the third station S3, as shown in FIG. 13, the adhesive dispenser 53 starts operation, the nozzle 53a is moved close to the barrel frame 12, adhesive G is discharged, and a predetermined amount of adhesive G is dropped in a groove section 12f of the barrel frame 12. The dropped adhesive G is flown evenly and filled between the surrounding wall section 11c of the planar-convex lens 11 and the inner surrounding wall of the first hollow section 12a of the barrel frame 12 to join the above two portions to each other (bonding step).

The position of the groove section 12f varies in the rotating direction depending on the position of the lens barrel 1. Therefore, the imaging device not shown detects the position and the CPU controls the nozzle 53a to move near the groove section 12f. The lens barrel 1 can be rotated so that the groove section 12f is placed in a certain position.

Moreover, it is preferable that heating by a heater is performed so that the adhesive G in the nozzle 53a is not cured.

The adhesive G is a thermal curing type, an optical curing type or a hybrid type of the above. After joining, heat or light is emitted on the adhesive G with a device not shown, and the adhesive G is cured.

Since the groove section 12f to drop the adhesive G is provided, it is possible to prevent the spreading of the adhesive G.

If the groove section 12f reaches the lens receiving section 12e, there is a possibility that the adhesive G flows to the planar surface section 11b of the planar-convex lens 11. Moreover, there is also a possibility that bubbles are formed in the adhesive G, resulting in undesirable appearance, and the joining point being insecure. Therefore, as shown in FIG. 2, it is preferable that the groove section 12f does not reach the lens receiving section 12e and stops at an intermediate position of the surrounding wall section 11c of the planar-convex lens 11.

Further, when a plurality of groove sections 12f are provided, there is a possibility that bubbles are formed in the portion where adhesive G flown from two groove sections 12f meet. Therefore, it is preferable that there is only one groove section 12f.

When the adhesive G is cured, the robot arm 32 holds the lens barrel 1, and the lens barrel 1 is conveyed to the fourth station S4.

[Fourth Station]

When the lens barrel 1 is moved to the fourth station S4, as shown in FIG. 3, the robot arm 32 holding the lens barrel 1 is extended, and the lens barrel 1 is placed on the lens barrel tray 43 one by one.

Here, the lens barrel tray 43 may be fixed, and the robot arm 32 may suitably move above the lens barrel tray 43, or the lens barrel tray 43 may move in a planar direction of front, back, left, and right so that the robot arm 32 can easily place the lens barrel 1.

The above described barrel frame tray 41, the lens tray 42, and the lens barrel tray 43 do not necessarily need to be trays, and each one can be taken out from a pod-like cartridge or, each one can be inserted in a cartridge.

When the barrel frame tray 41 and the lens tray 42 are empty and the lens barrel tray 43 is full, the imaging device can detect the above and automatically switch with other trays, or an alarm may urge an operator to switch with other trays.

The lens barrels 1 placed to fill the lens barrel tray 43 are sent to the curing chamber to be held for a certain amount of time in a certain temperature. With this, the adhesive G can be securely cured.

Then, the laser light is emitted on the lens barrel 1, and the examination of shifting, tilting, upper and lower position, etc. is performed on the barrel frame 12 of the planar-convex lens 11.

As described above, the feature of the present embodiment is that the planar-convex lens 11 moves from the suction pad 52a to the suction pad 51a. With this, as shown in the "A" portion of FIG. 14, even if the convex surface section 11a of the planar-convex lens 11 is sucked by the suction pad 52a in a tilted state, as shown in the "B" portion of FIG. 14, the planar surface section 11b of the planar convex lens 11 is sucked by the suction pad 51a and the tilt is corrected.

Regarding the suction pad 51a, as long as the planar surface section 11b of the planar-convex lens 11 can be held from the bottom, the planar-convex lens 11 does not necessarily have to be sucked.

Instead of the robot arm 32 continuing to hold the barrel frame 12 from the second station S2 to the fourth station S4, the robot arm 32 can release the hold of the barrel frame 12 when moved to the next station to fix the barrel frame 12 on a work space, and the robot arm 32 can be used only for conveying the barrel frame 12.

As long as the planar-convex lens 11 is a lens where one surface is a convex surface and the other surface is a planar surface, the planar-convex lens 11 may be a lens where a plurality of lenses are attached to each other. The planar surface does not have to be a perfect planar surface. The planar surface can be a surface close to a planar surface with an extremely small curvature compared to the convex surface, and the portion in contact with the first lens holding section (suction pad 51a) can be a substantial planar surface. It is preferable that the portion (out of effective optical surface) in contact with a lens receiving surface 120 is a planar surface.

The entire disclosure of Japanese Patent Application No. 2011-48618 filed on Mar. 7, 2011 including specification, claims, drawings and abstract are incorporated herein by reference in its entirety.

INDUSTRIAL APPLICABILITY

As described above, the present invention is suitable for the method of manufacturing a lens barrel by inserting a planar-convex lens in a barrel frame.

DESCRIPTION OF REFERENCE NUMERALS 1 lens barrel
11 planar-convex lens
11a convex surface section
11b planar surface section
11c surrounding wall section
12 barrel frame
12a first hollow section
12b, 12d opening section
12c second hollow section
12e lens receiving section
12f groove section
30 automatic assembling device
32 robot arm
41 barrel frame tray
42 lens tray
43 lens barrel tray
51 first suction device
51a, 52a suction pad
52 second suction device
53 adhesive dispenser
53a nozzle
G adhesive

The invention claimed is:

1. A manufacturing method of a lens barrel in which a first lens holding section which can hold a planar surface section of a planar-convex lens and a second lens holding section which can suck a convex surface section of the planar-convex lens are used to insert the planar-convex lens in a hollow section provided in a barrel frame, the manufacturing method comprising:
a first lens holding section protrusion step in which the first lens holding section is inserted from an opening section positioned at one end of the barrel frame to the hollow section to protrude the first lens holding section from an opening section positioned at the other end of the barrel frame;
a second lens holding section suction step in which the convex surface section of the planar-convex lens is sucked with the second lens holding section;
a first lens holding section contact step in which the planar surface section of the planar-convex lens is brought into contact with the first lens holding section after the first lens holding section protrusion step and the second lens holding section suction step;
a lens holding switching step in which suction of the convex surface section of the convex-planar lens is released by the second lens holding section, and the planar surface section of the planar-convex lens is held by the first lens holding section after the first lens holding section contact step; and
a barrel frame contact step in which the first lens holding section or the lens barrel is moved in an optical axis direction of the planar-convex lens so that a surrounding edge section of the planar surface section of the planar-convex lens is brought into contact with a lens receiving section provided in the hollow section of the barrel frame after the lens holding switching step.

2. The manufacturing method of a lens barrel of claim 1, wherein the second lens holding section suction step is performed after the first lens holding section protrusion step.

3. The manufacturing method of a lens barrel of claim 1, wherein the first lens holding section protrusion step is performed after the second lens holding section suction step.

4. The manufacturing method of a lens barrel of claim 1, wherein the second lens holding section suction step is performed simultaneously with the first lens holding section protrusion step.

5. The manufacturing method of a lens barrel of claim 1, wherein the planar-convex lens includes a side wall section formed between the convex surface section and the planar surface section parallel to an optical axis, and the side wall section is fitted to an inner surrounding wall of the hollow section of the barrel frame.

6. The manufacturing method of a lens barrel of claim 1, further comprising a bonding step in which the planar-convex lens is bonded to the barrel frame after the barrel frame contact step.

7. The manufacturing method of a lens barrel of claim 6, wherein the planar-convex lens includes a side wall section formed between the convex surface section and the planar surface section parallel to an optical axis, and adhesive is filled between the side wall section and an inner surrounding wall.

8. The manufacturing method of a lens barrel of claim 1, wherein the first lens holding section can suck the planar surface section of the planar-convex lens.

9. The manufacturing method of a lens barrel of claim 8, wherein vacuuming power of the first lens holding section is stronger than vacuuming power of the second lens holding section.

* * * * *